(12) United States Patent
Mao

(10) Patent No.: US 11,842,802 B2
(45) Date of Patent: Dec. 12, 2023

(54) EFFICIENT CLINICAL TRIAL MATCHING

(71) Applicant: KONINKLIJKE PHILIPS N.V., Eindhoven (NL)

(72) Inventor: Yong Mao, Hawthorne, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 596 days.

(21) Appl. No.: 15/580,353

(22) PCT Filed: Jun. 20, 2016

(86) PCT No.: PCT/IB2016/053646
§ 371 (c)(1),
(2) Date: Dec. 7, 2017

(87) PCT Pub. No.: WO2016/203457
PCT Pub. Date: Dec. 22, 2016

(65) Prior Publication Data
US 2018/0301205 A1    Oct. 18, 2018

Related U.S. Application Data

(60) Provisional application No. 62/181,787, filed on Jun. 19, 2015.

(51) Int. Cl.
G16H 10/20        (2018.01)
G16H 10/60        (2018.01)

(52) U.S. Cl.
CPC .............. *G16H 10/20* (2018.01); *G16H 10/60* (2018.01)

(58) Field of Classification Search
CPC ......... G16H 10/20; G16H 10/60; G06F 19/00
See application file for complete search history.

(56) References Cited

U.S. PATENT DOCUMENTS

2005/0097628 A1*  5/2005  Lussier ................... A61P 21/00
                                                         800/260
2005/0234740 A1   10/2005  Krishnan et al.
                        (Continued)

FOREIGN PATENT DOCUMENTS

| WO | 2014107549 A2 | 7/2014 |
| WO | 2014149972 A1 | 9/2014 |
| WO | 2015023674 A1 | 2/2015 |

OTHER PUBLICATIONS

Chen, et al., "The keyword-based and semantic driven data matching approach for assisting structuralizing the textual clinical documents", Biomedical Engineering and Informatics, 2010 3rd International Conference, vol. 6, pp. 2532-2535 (Abstract).
(Continued)

*Primary Examiner* — Jay M. Patel

(57) ABSTRACT

A patient-trial matching system (100) includes a structuralizer (102) configured to convert input non-structured patient health data and input non-structured clinical trial eligibility criteria into structured patient health data and structured clinical trial eligibility criteria by organizing a content of the non-structured data as known data elements. The patient-trial matching system further includes a semantic matcher (122) configured to match the structured patient health data and the structured clinical trial eligibility criteria based on user input matching criteria and outputs matched results. The patient-trial matching system further includes a ranking engine (126) configured to rank the matched results using ranking criteria (128), which include ranking patients matched to a clinical trial of interest in response to matching to find a group of trial patients and ranking clinical trials matched to a particular patient in response to matching to find a clinical trial.

19 Claims, 4 Drawing Sheets

(56) References Cited

U.S. PATENT DOCUMENTS

| | | | |
|---|---|---|---|
| 2008/0147441 A1* | 6/2008 | Kil | G06Q 40/08 705/2 |
| 2008/0167567 A1* | 7/2008 | Bashour | A61B 5/352 600/521 |
| 2008/0195600 A1* | 8/2008 | Deakter | G16H 10/60 |
| 2010/0195909 A1* | 8/2010 | Wasson | G06F 16/313 382/176 |
| 2010/0211411 A1* | 8/2010 | Hudson | G06Q 30/018 705/317 |
| 2010/0285082 A1* | 11/2010 | Fernandez | A61B 5/7264 506/13 |
| 2011/0082712 A1* | 4/2011 | Eberhardt, III | G16Z 99/00 705/4 |
| 2012/0035954 A1 | 2/2012 | Yeskel | |
| 2012/0323132 A1* | 12/2012 | Warner | G16H 40/63 600/509 |
| 2013/0238359 A1 | 9/2013 | Carter et al. | |
| 2013/0332191 A1* | 12/2013 | Hoffman | G06Q 30/02 705/3 |
| 2014/0046926 A1* | 2/2014 | Walton | G06F 16/20 707/710 |
| 2014/0181128 A1 | 6/2014 | Riskin et al. | |
| 2014/0316793 A1* | 10/2014 | Pruit | G16H 10/20 705/2 |
| 2014/0359422 A1 | 12/2014 | Bassett, Jr. et al. | |
| 2015/0012222 A1* | 1/2015 | Warner | A61B 5/316 702/19 |
| 2015/0073830 A1 | 3/2015 | Hill et al. | |
| 2016/0314280 A1* | 10/2016 | Fusari | G06F 19/3418 |
| 2016/0364544 A1* | 12/2016 | Das | A61B 5/02055 |
| 2017/0112401 A1* | 4/2017 | Rapin | A61B 5/7203 |
| 2019/0311787 A1* | 10/2019 | Graiver | G16H 10/60 |

OTHER PUBLICATIONS

Patel, et al, "TrialX: Using semantic technologies to match patients to relevant clinical trials based on their Personal Health Records", Web Semantics: Science, Services and Agents o the World Wide Web, vol. 8, Issue 4, Nov. 2010, pp. 342-347 (Abstract).

* cited by examiner

EFFICIENT CLINICAL TRIAL MATCHING

CROSS-REFERENCE TO PRIOR APPLICATIONS

This application is the U.S. National Phase application under 35 U.S.C. § 371 of International Application No. PCT/IB2016/053646, filed on Jun. 20, 2016, which claims the benefit of U.S. Provisional Application Ser. No. 62/181,787, filed Jun. 19, 2015. These applications are hereby incorporated by reference herein, for all purposes.

FIELD OF THE INVENTION

The following generally relates to the clinical trial matching and more particularly to efficient clinical trial matching.

BACKGROUND OF THE INVENTION

The healthcare industry has relied on clinical trials for pre-drug/medical-device/treatment research. A clinical trial, generally, is a government-regulated experiment done in clinical research, for example, on participants (e.g., humans, animals, etc.) to answer questions about new treatments such as pharmaceuticals, medical devices, etc. For a clinical trial to succeed, a sufficient number of patients must participate. Clinical trials have failed because sponsors have not been able to recruit a sufficient number of patients within foreseen time and budget. For example, in one instance, the average recruitment rate for all trials is lower than 50%, and patient recruitment delays clinical trials around 4.6 months. Examples of matching approaches are discussed in U.S. Pat. No. 7,937,275-B2, U.S. Pat. No. 7,904,313-B2, U.S. Pat. No. 7,711,580-B1, U.S. Pat. No. 7,499,866-B2 and U.S. Pat. No. 8,095,389-B2.

These approaches involve understanding and sorting out clinical trial eligibility criteria with pre-defined rules and collecting structured patient data through online survey. U.S. Pat. No. 8,095,389-B2 also addresses handling molecular-level data required by both personal health record (PHR) and trial eligibility criteria. In general, workflow begins from identifying a molecular signature, which could discriminate pre-drug responders and non-responders. Then the signature is used to predict/match potential trial candidates, who may have response to the pre-drug. A rule-based matcher, implemented as a computer program, processes the data and provides a preliminary/refined candidate patient/trial list. Clinical information for these candidates is collected through pre-designed survey webserver to compare with the left clinical trial eligibility criteria for the specific pre-drug.

The above systems deal with structured data through manually curated rules embedded in information retrieval programs. These ad-hoc designed rules can cover simple aspects, but cannot cover sematic aspects described in clinical trial eligibility criteria and link this to information from the patient PHR consistently. It may further cause false positives in reporting candidate list. Updating these rule-based systems to follow up the up-to-date patient description and clinical trial eligibility criteria would be also problematic. Meanwhile, the rules used in one system might not be portable onto the data collected by other systems. Since an increasing number of clinical trials are designed with requirement on status of companion biomarkers, software component to address matching on this part between PHR and clinical trial criteria has not been included in most of current available systems. Current available systems do not have comprehensive prioritization modules. Therefore, there is an unresolved need for another approach.

SUMMARY OF THE INVENTION

Aspects of the present application address the above-referenced matters and others.

According to one aspect, a patient-trial matching system includes a structuralizer configured to convert input non-structured patient health data and input non-structured clinical trial eligibility criteria into structured patient health data and structured clinical trial eligibility criteria by organizing a content of the non-structured data as known data elements. The patient-trial matching system further includes a semantic matcher configured to match the structured patient health data and the structured clinical trial eligibility criteria based on user input matching criteria and outputs matched results. The patient-trial matching system further includes a ranking engine configured to rank the matched results using ranking criteria, which include ranking patients matched to a clinical trial of interest in response to matching to find a group of trial patients and ranking clinical trials matched to a particular patient in response to matching to find a clinical trial.

In another aspect, a method for patient-trial matching includes converting input non-structured patient health data and input non-structured clinical trial eligibility criteria into structured patient health data and structured clinical trial eligibility criteria by organizing a content of the non-structured data as known data elements. The method further includes matching the structured patient health data and the structured clinical trial eligibility criteria based on user input matching criteria and outputs matched results. The method further includes ranking the matched results using ranking criteria that includes ranking patients matched to a clinical trial of interest in response to matching to find a group of trial patients and ranking clinical trials matched to a particular patient in response to matching to find a clinical trial.

In another aspect, a computer readable storage medium is encoded with computer readable instructions, which, when executed by a processor of a computing system, causes the processor to: convert input non-structured patient health data and input non-structured clinical trial eligibility criteria into structured patient health data and structured clinical trial eligibility criteria by organizing a content of the non-structured data as known data elements, match the structured patient health data and the structured clinical trial eligibility criteria based on user input matching criteria and outputs matched result, and rank the matched results using ranking criteria that includes ranking patients matched to a clinical trial of interest in response to matching to find a group of trial patients and ranking clinical trials matched to a particular patient in response to matching to find a clinical trial.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
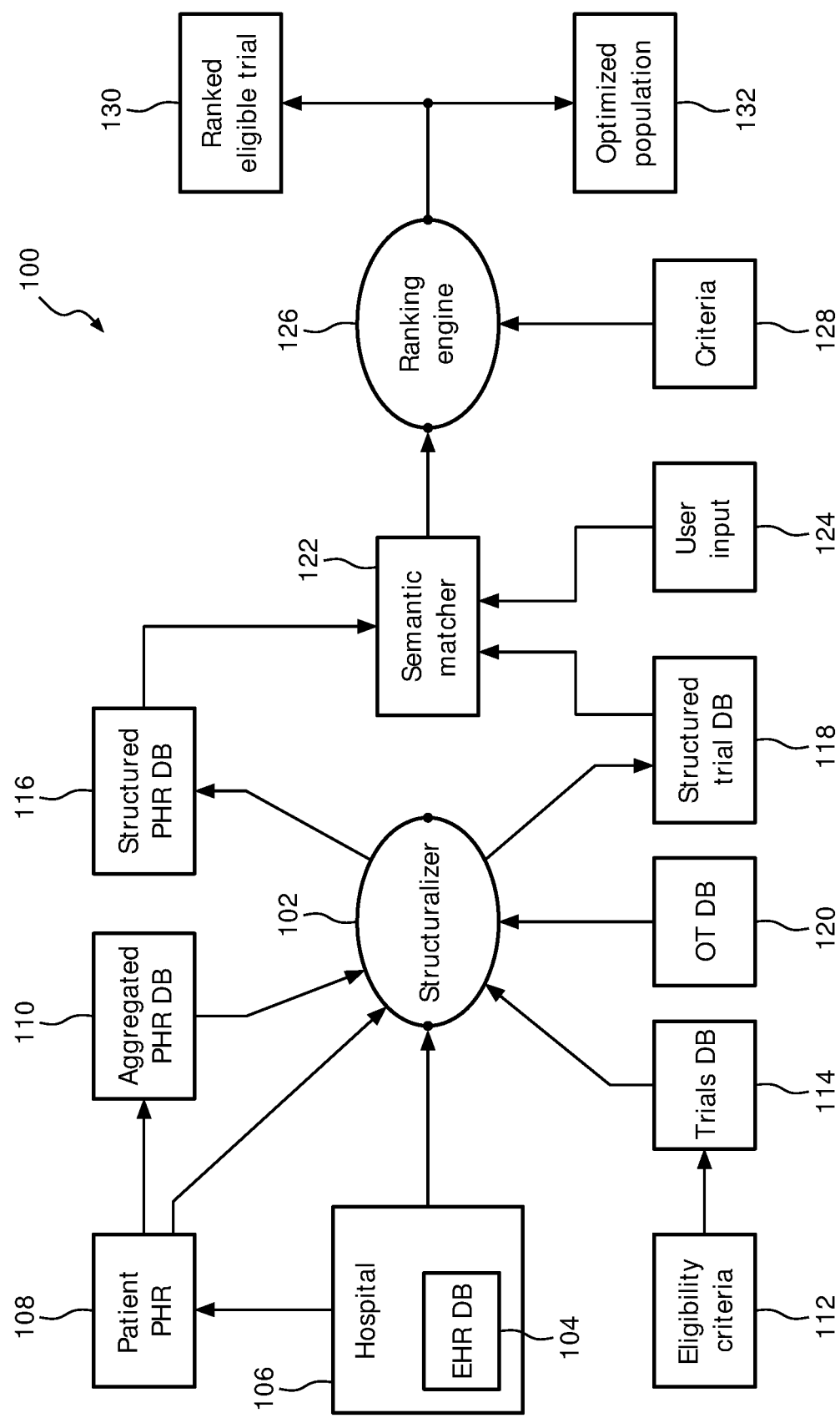
FIG. 1 schematically illustrates an example patient-trial matching system.

FIG. 1 illustrates a patient-trial matching system 100. The patient-trial matching system 100 includes a structuralizer 102. The structuralizer 102 is configured to convert input non-structured data into structured data. An example of non-structured data is the following sentence "John Doe is a six foot tall sixty years old." In one non-limiting instance, structuralizing this sentence would produce the following structured data: name=John Doe; height=6'0"; age=60. In general, the structuralizer 102 employs a predetermined data model to analyze non-structured data and organize certain content in the non-structured data (name, height and age in the above example) into known data elements.

In the illustrated embodiment, the structuralizer 102 structuralizes patient data and trial data. In this example, the patient data is stored in an electronic health record (EHR) database (DB) 104 at a hospital 106, a device 108 storing a PHR which can be retrieved from the EHR DB 104 and/or elsewhere), and/or an aggregated PHR DB 110, which may be a third party storage repository. An EHR, in one instance, includes a virtual health record (VHR) and/or electronic medical record (EMR) and contains medical as well as personal health data (e.g., medical and non-medical).

The trial data includes trial criteria 112 stored in a trial DB 114. Trial criteria 112 includes eligibility criteria such as age, gender, medical history, current health status, particular type and stage of some disease condition, molecular features, (e.g. mutations, expressions,—well-structured), etc. Clinical trial data are publicly available through government agencies, etc. Structuralized patient data and clinical trial data are respectively stored in a structured PHR DB 116 and a structured trial DB 118.

Figure 2:
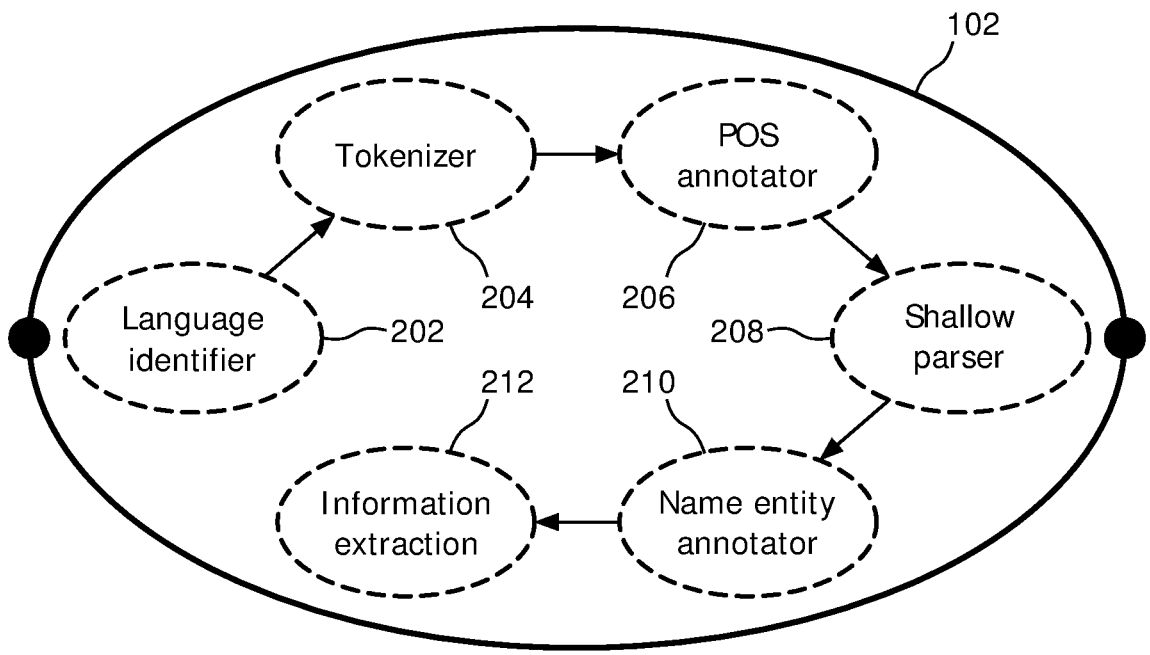
FIG. 2 schematically illustrates an example structuralizer of the patient-trial matching system.

FIG. 2 illustrates an example of the structuralizer 102 in connection with an oncology example. In this example, the structuralizer 102 employs natural language processing (NLP) and comprises modules for language identification (a language identifier 202), tokenization (a tokenizer 204), part-of-speech (POS) annotation (a POS annotator 206), parsing (a shallow parser 208), a name entity identification (a name entity annotator 210), and information extraction (an information extraction 212). Other approaches are also contemplated herein.

Returning to FIG. 1, the patient-trial matching system 100 further includes an ontology/terminology (OT) DB 120. The OT DB 120 stores standardization of genomic and clinical information. The structuralizer 102 employs the data in the OT DB 120 to structuralize the patient data and the clinical trial data. It is to be appreciated that the structuralizer 102 can update the structured trial DB 118 based on a schedule, on demand (e.g., when data in the trials DB 114 is altered), automatically, manually, periodically, etc. Furthermore, the data in the OT DB 120 can likewise and/or otherwise be updated.

The patient-trial matching system 100 further includes a semantic matcher 122. The semantic matcher 122 matches patient information stored in the structured PHR DB 116 and the clinical trial information stored in the structured trial DB 118. In one instance, the semantic matcher 122 employs a search engine to match patient data and clinical trial data and hence patients and clinical trials. The matching, e.g., is based on user identified criteria, where the semantic matcher 122 is configured to receive user input 124, which identifies patient and/or trial characteristics of interest, and employ this input during matching. An example of a trial characteristic is treatment, prevention, screening, diagnosis, etc.

In one instance, the semantic matcher 122 includes and employs a genomic aberration detection system that is capable of automatically detecting genomic or transcriptomic aberrations. Examples of suitable aberrations include, but are not limited to, single nucleotide polymorphisms, copy number polymorphisms, gene fusions, differentiated expression of a certain gene/protein, differential methylation status of a gene. The semantic matcher 122 matches the detected aberrations from the structured PHR DB 116 with the clinical trial information stored in the structured trial DB 118.

An example of a genomic aberration detection system is PAPAyA, or Physician Accessible Preclinical Analytics Application. An example of PAPAyA is described in BMC Bioinformatics, Volume 10 Supplement 9, 2009: Proceedings of the 2009 AMIA Summit on Translational Bioinformatics; Philips Research North America, 345 Scarborough Road, Briarcliff Manor, N.Y. 10510, USA. Other genomic aberration detection system and/or detection systems are also contemplated herein.

Figure 3:
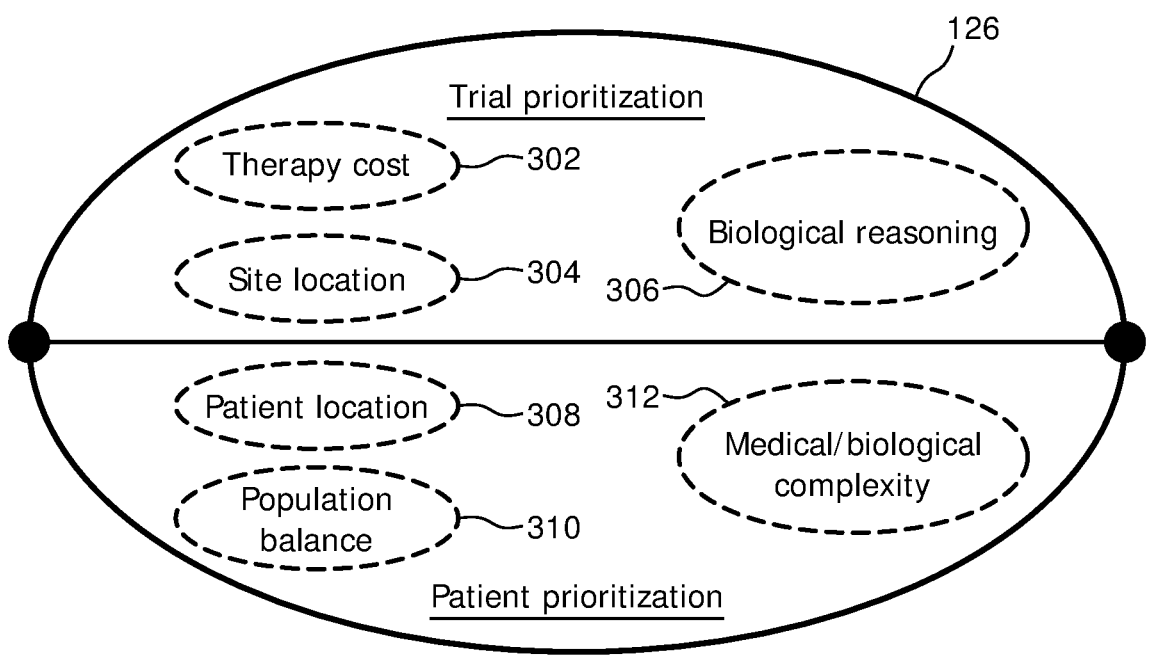
FIG. 3 schematically illustrates an example ranking engine of the patient-trial matching system.

The patient-trial matching system 100 further includes a ranking engine 126. The ranking engine 126 ranks the matched results based on ranking criteria 128. FIG. 3 illustrates an example of the ranking engine 126. In this example, trials are prioritized based on therapy cost 302, site location 304, and biological reasoning 306. Patients are prioritized based on patient location 308, population balance 310, and medical/biological complexity 312. Additional and/or alternative criteria are also contemplated herein. The ranking engine 126 outputs ranked eligible trials 130 and/or optimized population 132. This data is in electronic format and can be saved as a file, displayed via a monitor, conveyed to another computing device, etc.

Returning to FIG. 1, it is to be understood that the system 100 and/or a sub-set of its components (e.g., the structuralizer 102, the semantic matcher 122, the ranking engine 126, etc.) can be implemented by a computer(s) with at least one processor (e.g., a microprocessor, a central processing unit, a controller, etc.) configured to execute at least one computer readable instruction stored in non-transitory computer readable storage medium (which excludes transitory medium) such as physical memory and/or other non-transitory medium. In one instance, the computer is a configured computer, and not a generic computer. For example, the configured computer additionally includes hardware and/or software configured to improve efficiency. For example, the computer can be a clinical decision support (CDS) system.

In one instance, the system 100 is a software module of a hospital information system (HIS) and/or as independent web-service software residing on secured cloud, etc. In an HIS, the system 100 serves the hospital. The hospital can further provide services to the third parties, trial sponsors, the hospital and/or the patient. As a web-service, the system 100 could directly serve the patient, the hospital, the trial sponsor, the third party, etc. In either case, the system 100 can be a subscription based free or pay for service system. As a subscription service, the patient-trial matching system 100 further includes an authorization and/or validation system that first verifies the user is subscribed before allowing the user to use the invoke a search.

Users of the system 100 include, for example, a patient population recruiter looking to recruit patients for their clinical trials, a clinician providing a service to a patient, and a patient looking to find a cure. For the patient population recruiter, the system 100 is accessed, e.g., via the HIS system and/or the web-server. A user first registers, and then is provided with the capability to execute the patient search for particular trial. In this instance, the system 100 screens available patients with informed consent and provides a list of prioritized/matched patients within the constraints set by user.

For a clinician looking for a trial for a patient, once the service is ordered according to conditions set for prioritization, an electrical report is fed back onto user's graphic user interface and provides a prioritized list of clinical trials, which match to the particular patient. For a patient looking for a trial, the user confirms and agrees to have his/her PHR uploaded to activate the service. A report about prioritized clinical trials is then provided according to the constraints set by the user. This report can be shared with the patient's care manager and/or care provider, e.g., so that the doctor and patient can discuss and decide which options are most suitable for this patient.

Figure 5:
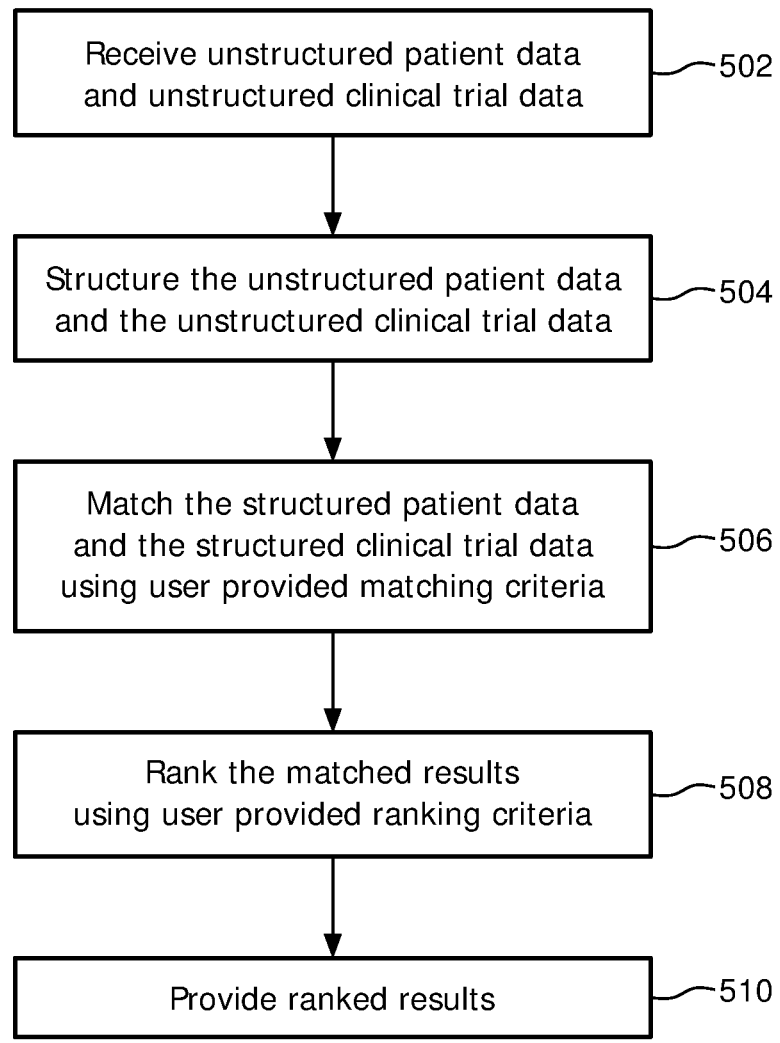
FIG. 5 illustrates an example method in accordance with an embodiment herein.

FIG. 5 illustrates an example method in accordance with an embodiment herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 502, unstructured patient data and unstructured clinical trial data are received. As described herein, this data can be received from the EHR 104, the device 108, the aggregated PHR DB 110, the clinical trials DB 114, and/or elsewhere.

At 504, the unstructured patient data and the unstructured clinical trial data are structuralized, creating structured patient data and structured clinical trial data, as described herein and/or otherwise.

At 506, the structured patient data and the structured clinical trial data are matched, as described herein and/or otherwise.

At 508, the matched structured patient data and the structured clinical trial data are ranked, as described herein and/or otherwise.

Optionally, the system 100, in response to the matched and/or ranked data, invokes another device (e.g., a cell phone, a pager, etc.) to notify a user of the other device of a match and/or the rankings.

The above may be implemented by way of computer readable instructions, which when executed by a computer processor(s), cause the processor(s) to carry out the described acts. In such a case, the instructions can be stored in a computer readable storage medium associated with or otherwise accessible to the relevant computer. Additionally or alternatively, one or more of the instructions can be carried by a carrier wave or signal.

The following illustrates example case scenarios.

Clinical Expert

A medical oncologist, Dr. A, wants to find a suitable clinical trial for his patient, B, with late-stage cancer and trying to find a treatment. Dr. A could activate the system 100 to directly access all available clinical and lab-test data including genomic information for patient B from inside HIS system. At the backend, the system 100 is synchronous with clinical trial info sources, so that all related info is up-to-date and structuralized according to clinical/pre-clinical terminology systems by the structuralizer 102. From FIG. 2, the structuralizer 102 comprises modules for language identification, tokenization, part-of-speech (POS) annotation, name entity identification and information extraction. In this example, an inner database instance is maintained to store the structuralized up-to-date clinical trial info.

By setting the constraint as treatment, data for treatment oriented clinical trials is marked as the targeted subset. Meanwhile, patient B's relevant info will also be structuralized by the structuralizer 102. Since data from matched patients would normally have more items than those listed in clinical trials, structured eligibility criteria are used as query constraints in a semantic matcher, which could match information along the ontology structures. For example, a clinical trial might want a patient diagnosed with brain tumor. If the patient was marked with glioblastoma multiforme (GBM), the semantic matcher 122 could identify GBM is a descendent of brain tumor semantically and match them with each other. With a list of matched clinical trials reported from the semantic matcher 122, the ranking engine 126 prioritize these trials according to the (or default) conditions set by the user.

In this example, the ranking is based on information from more specific information such as gene name and variant (or mutation) to clinical phenotype. Next, the priority would be based on patient's preferences such as distance to the trial site, side effects, etc. For example, the user could search all clinical trials available within 50 miles (or within a distance to a specific place) and with trial cost less than $2,000. Since different clinical trials or their arms might target different biological mechanisms, e.g. mutations on BRAF or EGFR, if patient has all of these mutations, he/she might have multiple matching clinical trials either targeting BRAF or EGFR. Determining which mutation is more likely to be a driver is the key for prioritizing trials. Population-scale mutation prevalence, sequence conservation, etc. would be provided to the user as evidence for this process.

In one instance, if the patient bares both BRAF_V600E and EGFR_G1158V, a trial targeting BRAF would be ranked higher than trials targeting other genes. Clinical evidence from previous publications about trials and association of the variant with response to prioritize higher a trial with a variant and drug for which there is already evidence of increased response can also be considered. The opposite may also happen, to deprioritize the trial (and respective gene and variant) for which the reported response was decreased.

Patient Seeking Information on Clinical Trials

Another embodiment begins with the patient's genomic aberrations. If a full exome (or targeted exome, which includes a panel of actionable cancer-related genes, or whole genome -) sequence data is available, the somatic mutations from the patient's tumor are first matched to the mutations listed in all the structuralized stored information from all the clinical trials. A patient is matched against all the standard clinical trials with a standard design. In addition, all the clinical trials that have the "basket" trial design, may be recruiting for the same genomic aberration. In this case, the patient will be enrolled in the "basket" specific for his/her tumor type. In the case of an umbrella design, first the patient's tumor type is matched, using the extracted histology information and then enrolled under the umbrella for the specific drug for that indication (histology-based).

Clinical Trial Organization

In another embodiment, a clinical trial matching service provider, clinical site A, has reached an agreement with one or more pharmaceutical companies or CRO, B, to look for patient populations matching their specific clinical trials.

Inside the system 100, dedicated database instances are set to store all patients' up-to-date structuralized info pre-parsed by structuralizer 102 so that the matching process is accelerated. For an aimed clinical trial from B, its eligibility criteria will be parsed by the structuralizer 102 and further used as query constraint to check available patient population with sematic matcher. After specific patient population queried out, patients will be first prioritized according to clients' specific requirements. For example, B wants <=50 patients from A, patients' distance to A is within 50 miles, patient population's age should be well balanced between male and female, etc. Once A could find a patient population with size >=50, further prioritization could be done for customers, according to medical/biological complexity found on the targeted patients.

Composite Filters for Clinical Trial Matching

To match a patient to a clinical trial, before applying genomic filters, there are a number of fields that could be filtered to shrink down the screening scale of clinical trial data. For example, one aspect of interest is that the status of the potential clinical trial needs to be marked with "recruiting" and mostly "Interventional" since late stage cancer patients are expected to be enrolled. Candidate trials should be marked with a study design as "Efficacy" and with primary purpose for "Treatment." With the structuralizer 102, specific requirements for different arms of a trial are parsed out, including common demographic and eligibility/ineligibility criteria.

For example, for the phase 2 arm B of trial NCT01877811, the inclusion criteria parsed out would require patient with (1) confirmed stage IIIC and IV advanced unresectable cutaneous melanoma; (2) Age>18; (3) BRAF V600E or BRAF V600K mutation given by a CLIA lab or with fresh tissue for test; (4) prior treatment with only 1 BRAF inhibitor or MEK inhibitor monotherapy; (5) with measurable disease and documented progression on or after last prior treatment according to RECIST 1.1 criteria; (6) ECOG performance status=2; (7) no systemic anticancer therapy or investigational agent given within 3 weeks; (8) no major surgery within 21 days; (9) no radiotherapy within 2 weeks; (10) no central nervous system (CNS) metastases; (11) QTc<470 msec; (12) no major active infection and no need for antibiotics; (13) No other severe or unstable medical condition etc.

Figure 4:
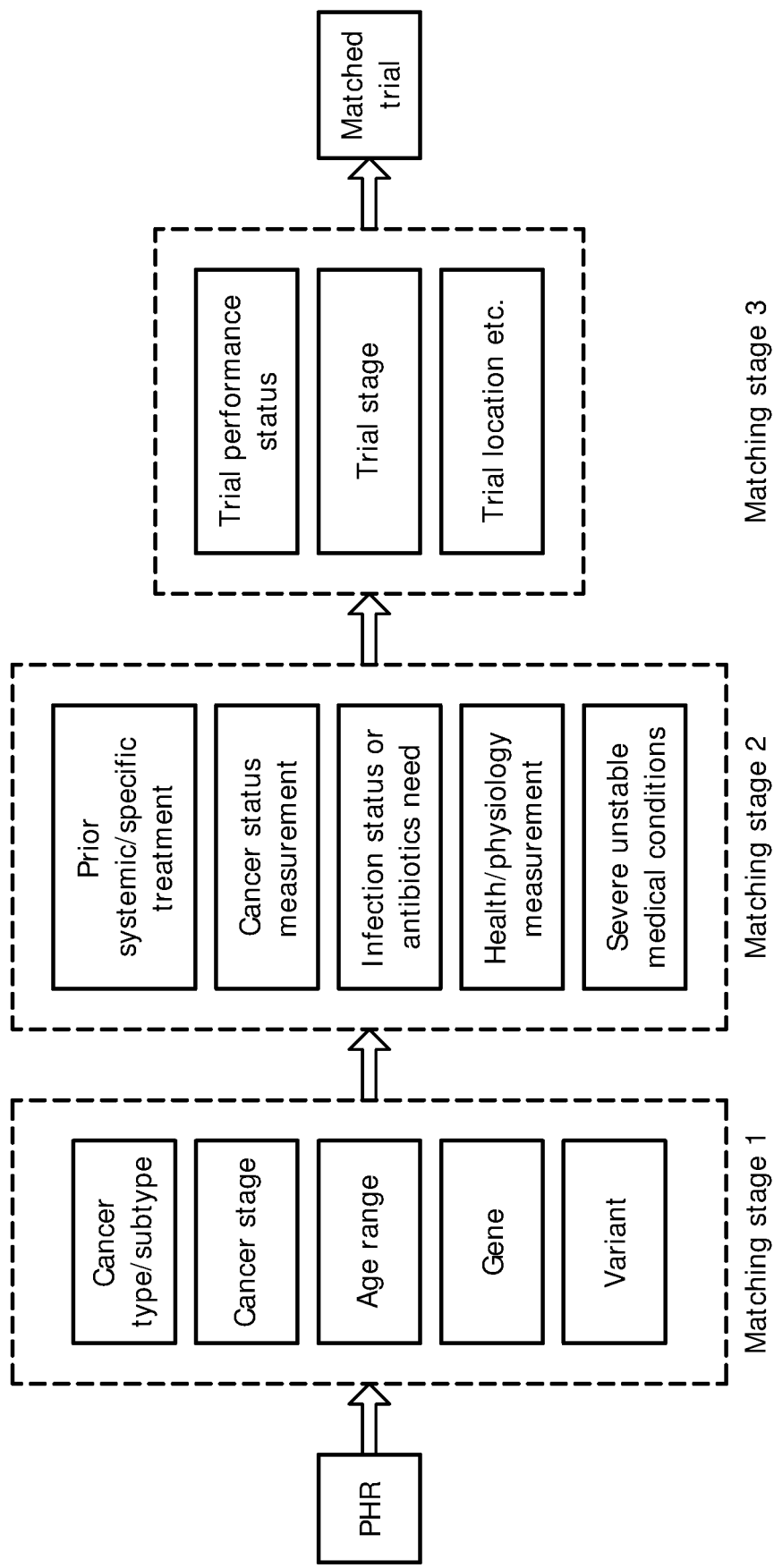
FIG. 4 illustrates a general process for trial matching.

After the patient's PHR is parsed and compared with the structured trial info, if the patient could match all the aforementioned requirement, the trial NCT01877811 will be saved as a candidate trial for the patient. After all available trials were collected for the patient, they will be ranked according to their ongoing stage, driverness of the corresponding genomic abberations, location of trial site etc. A more general process for trial matching is shown in FIG. 4.

Further details on the genomic-aberrations-based clinical trial matching are discussed next.

Exome Based Clinical Trial Matching

In this scenario, exome sequencing data will be required for patients in corresponding applications. A PAPAyA pipeline is first applied onto these exome sequencing data. All single nucleotide variants and structural variants with high confidence score, including gene fusion, copy number aberrations, are identified and annotated. For each mutation, information, like corresponding gene symbol, transcript ID and possible amino acid substitution, are mapped out and added to the annotation. The mutation profile will be further affiliated with patient PHR and saved into a database.

For an enrolling clinical trial with requirement for a particular mutation on candidate's genetic profile, like BRAF V600E/K, the system 100 scans on all patients' genetic profiles for such match, and then further on match between the patient PHR and the other (in)eligibility criteria. For a patient, who wants to find a matched clinical trial, since normally each clinical trial will target only a small part (or even none part) of the candidate's mutations, the system 100 iteratively scans all available trials with particular requirement on mutations for a specific gene. For clinical trials targeting a part of patient's mutations, the data is further filtered by match between patient's PHR and the other (in) eligibility criteria.

A patient with a highly mutated tumor sample can be a candidate for multiple trials, each of which has requirements on different specific set of mutations. In such scenario, trial-specific mutation's prevalence accumulated in PAPAyA knowledge-base will be used as the first principal to determine which trial would be prioritized on top. If multiple trials' mutations' prevalence is similar, the importance for mutations will be prioritized according to (1) their functional impact on corresponding proteins; (2) the importance of the corresponding proteins for particular cancer type; (3) the importance of the corresponding pathways in which the gene plays a significant role. Features corresponding to these three aspects will be accumulated from TCGA data portal, third-party software (e.g. SIFT, Polyphen-2). With a group of comprehensively collected features, a classification model is built to provide probability for prioritizing all mutations. The detailed modeling process could be combination of any type of classifier and feature selection method. E.g. Naïve Bayes classifier) combined with features preselected by ranksum, a univariate statistical method. The number of features finally involved in the model is determined by its superior performance on cross-validation and/or independent validation set.

Genomic Aberrations Based Clinical Trial Matching

In this scenario, patient will be required to provide his/her genomic aberration profile besides PHR to the system 100. Since the genomic aberrations might happen across the whole genome, the PAPAyA annotation component is first used to translate these mutations into on-exome and off-exome ones. With mutations that exist on protein coding regions (with exome sequencing), the above described method is used for clinical trial matching. Mutations which belong to non-coding regions, will not be translated into protein, and therefore their description info (genome coordinate plus changes) will be directly used to guide matching search. These mutations might involve, but not limited to, long lon-coding RNAs, enhancers and other types of important regulatory mechanisms. For a patient who wants to find a trial, if multiple trials are available for the same patient, their targeting mutations' prevalence will be still used as first principal to prioritize trials. If multiple trials' targeted mutations' prevalence is similar, further knowledge information pulled out from databases, e.g. ensemble, will be further used for prioritizing mutations involving any important biological regulatory mechanism. Also, clinical trials targeting protein coding mutations will be prioritized higher than trials targeting non-coding mutations, as currently there is more knowledge and evidence about the functional impact of protein coding mutations. And for the latter, clinical trials targeting mutation hotspots will be prioritized on top of the others.

Gene Expression Based Clinical Trial Matching

In this scenario, patient will be required to provide his/her RNA-SEQ data or gene expression profile besides PHR to the system 100. The main purpose is to find a trial a group of candidate patients. Many clinical trials require candidates with activated signal on particular gene expression signature, which is either developed by mining retrospective data or by an adaptive learning process embedded in clinical trial. For RNA-SEQ data, PAPAyA pipeline will align, sort all raw sequencing reads, estimate initial gene expression and get the signal normalize for particular signature. For expression profile, PAPAyA will normalize the data to remove batch effect. Since the signature has already been defined, with the extracted gene expression as input for the signature, an activation score will be calculated to judge if the patient is with a score with the range defined in the clinical trial. Further match between the patient's PHR and the other part of the eligibility criteria will determine if the patient is a right candidate.

Pathway-Model Based Clinical Trial Matching

In this scenario, there is no clinical trial available to target any of important mutations from a particular patient's genetic profile. In order to find for the patient a potential clinical trial, the process begins by taking into account all genomic (or transcriptomic or epigenomic) aberrations and performing pathway (or gene sets) enrichment test (e.g. hypergeometric test) to identify significantly disrupted pathways with the pathway models accumulated in PAPAyA system based on either one of patient's mutation profile and gene expression profile or both. By using PAPAyA knowledge base, targets for treatment/drugs/pre-drugs involved in clinical trials will be mapped out and onto the significantly disrupted pathways. Clinical trials with a focus on improving treatment efficacy for the patient's disease which at the same time are targeting the significantly disrupted pathways will be sorted and prioritized on top of the list for the patient.

The approach described herein is applicable to enable an organization, like hospitals/pharms, to find and prioritize candidate patients for their clinical trials in an agile and large-scale way, and/or a patient to find and prioritize suitable clinical trials globally and in time through webservice. Although discussed herein in the context of oncology, it can also be used in non-oncology applications such as cardiovascular, diabetes and/or other types of diseases.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention claimed is:

1. A natural language processing patient-trial matching system, comprising:
one or more processors configured to:
convert, using data in an ontology/terminology database, non-structured text-based patient health data received from an electronic health record database and/or a patient computing device and non-structured text-based clinical trail eligibility criteria into structured text-based patient health data and structured text-based clinical trail eligibility criteria by:
identifying language in the non-structured text-based patient health data and the non-structured text-based clinical trail eligibility criteria;
tokenizing the identified language;
annotating the tokenized language with parts of speech;
parsing the annotated language, based at least in part on the parts of speech;
annotating the parsed language with name entities; and
extracting information from the annotated language, based at least in part on the name entities;

match the structured text-based patient health data and the structured text-based clinical trial eligibility criteria based on matching criteria and output matched results;
rank the matched results using ranking criteria to prioritize the matched results, wherein ranking the matched results includes ranking patients matched to a clinical trial of interest based at least on therapy cost, site location, and biological reasoning, and ranking clinical trials matched to a particular patient based at least on patient location, population balance, and medical/biological complexity, wherein the population balance is based on demographic information including age and gender of the matched patients;
based on the ranking of the matched results, identify highest ranked patients matched to the clinical trial of interest as an optimized group of trial patients for the clinical trial of interest, and identify a highest ranked clinical trail matched to the particular patient as an eligible clinical trial;
automatically update the ontology/terminology database; and
invoke a device to provide a notification to a user of at least one of the matched results, the optimized group of trial patients for the clinical trial of interest, or the eligible clinical trial for the particular patient.

2. The patient-trial matching system of claim 1, wherein the processor employs a predetermined data model to convert the non-structured text-based data to structured data by organizing a content of the non-structured text-based data as known data elements.

3. The patient-trial matching system of claim 1, further comprising:
a structured patient health record database that stores the structured text-based patient health data; and
a structured clinical trial database that stores the clinical trial eligibility criteria.

4. The patient-trial matching system of claim 1, wherein the electronic health record database is located at a hospital.

5. The patient-trial matching system of claim 1, further comprising, at least one of:
an aggregated patient health record database that stores non-structured text-based patient health records for multiple different patients.

6. The patient-trial matching system of claim 1, the processor comprising:
a search engine that matches the patient health data and the clinical trial eligibility criteria.

7. The patient-trial matching system of claim 6, wherein the clinical trial eligibility criteria includes a characteristic from one of a treatment, a prevention, a screening, or a diagnosis.

8. The patient-trial matching system of claim 7, wherein the processor matches includes a genomic aberration detection system configured to detect at least one of genomic or transcriptomic aberrations.

9. The patient-trial matching system of claim 8, wherein the genomic aberration includes at least one of a single nucleotide polymorphisms, a copy number polymorphisms, a gene fusion, a differentiated expression of a certain gene/protein, or a differential methylation status of a gene.

10. The patient-trial matching system of claim 8, wherein the genomic aberration detection system includes a Physician Accessible Preclinical Analytics Application.

11. The patient-trial matching system of claim 1, further comprising:
a configured computer that comprises the one or more processors.

12. A method for patient-trial matching using natural language processing, the method comprising:
- converting, with a processor using data in an ontology/terminology database, non-structured text-based patient health data received from an electronic health record database and/or a patient computing device and non-structured text-based clinical trial eligibility criteria into structured text-based patient health data and structured text-based clinical trial eligibility criteria, wherein the converting comprises:
- identifying language in the non-structured text-based patient health data and the non-structured text-based clinical trial eligibility criteria;
- tokenizing the identified language;
- annotating the tokenized language with parts of speech;
- parsing the annotated language, based at least in part on the parts of speech;
- annotating the parsed language with name entities; and
- extracting information from the annotated language, based at least in part on the name entities;
- matching, with the processor, the structured text-based patient health data and the structured text-based clinical trial eligibility criteria based on matching criteria and outputting matched results; and
- ranking, with the processor, the matched results using ranking criteria to prioritize the matched results, wherein ranking the matched results includes ranking patients matched to a clinical trial of interest based at least on therapy cost, site location, and biological reasoning, and ranking clinical trials matched to a particular patient based at least on patient location, population balance, and medical/biological complexity, wherein the population balance is based on demographic information including age and gender of the matched patients;
- based on the ranking of the matched results, identifying highest ranked patients matched to the clinical trial of interest as an optimized group of trial patients for the clinical trial of interest, and identifying a highest ranked clinical trail matched to the particular patient as an eligible clinical trial;
- automatically updating the ontology/terminology database; and
- invoking a device to provide a notification to a user of at least one of the matched results, the optimized group of trial patients for the clinical trial of interest, or the eligible clinical trial for the particular patient.

13. The method of claim 12, further comprising:
- storing and retrieving the structured text-based patient health data from a structured patient health record database; and
- storing and retrieving the structured text-based clinical trial eligibility criteria from a structured clinical trial eligibility criteria database.

14. The method of claim 13, matching the structured text-based patient health data and the structured text-based clinical trial eligibility criteria comprises:
- employing a search engine to search the structured patient health record database and the structured clinical trial eligibility criteria database and matching the structured text-based patient health data and the structured text-based clinical trial eligibility criteria based on results of the search.

15. The method of claim 12, the matching the structured text-based patient health data and the structured text-based clinical trial eligibility criteria comprises detecting at least one of aberration in the structured text-based patient health data and matching the aberration with the structured clinical trial eligibility criteria.

16. The method of claim 15, wherein the aberration includes at least one of a single nucleotide polymorphisms, a copy number polymorphisms, a gene fusion, a differentiated expression of a certain gene/protein, or a differential methylation status of a gene.

17. A non-transitory computer readable storage medium encoded with computer readable instructions, which, when executed by a processor of a computing system, causes the processor to:
- convert, using data in an ontology/terminology database, non-structured text-based patient health data and input non-structured text-based clinical trial eligibility criteria into structured text-based patient health data and structured text-based clinical trial eligibility criteria by:
- identifying language in the non-structured text-based patient health data and the non-structured text-based clinical trial eligibility criteria;
- tokenizing the identified language;
- annotating the tokenized language with parts of speech;
- parsing the annotated language, based at least in part on the parts of speech;
- annotating the parsed language with name entities; and
- extracting information from the annotated language, based at least in part of the name entities;
- match the structured text-based patient health data and the structured text-based clinical trial eligibility criteria based on matching criteria and outputs matched results;
- rank the matched results using ranking criteria to prioritize the matched results, wherein ranking the matched results includes ranking patients matched to a clinical trial of interest based at least on therapy cost, site location, and biological reasoning, and wherein ranking clinical trials matched to a particular patient based at least on patient location, population balance, and medical/biological complexity, wherein the population balance is based on demographic information including age and gender of the matched patients;
- based on the ranking of the matched results, identify highest ranked patients matched to the clinical trial of interest as an optimized group of trial patients for the clinical trial of interest, and identify a highest ranked clinical trail matched to the particular patient as an eligible clinical trial;
- automatically update the ontology/terminology database; and
- invoke a device to provide a notification to a user of at least one of the matched results, the optimized group of trial patients for the clinical trial of interest, or the eligible clinical trial for the particular patient.

18. The patient-trial matching system of claim 1, wherein ranking the matched results using the ranking criteria includes prioritizing or deprioritizing each clinical trial of the clinical trials based on an increased or decreased drug response associated with the particular patient.

19. The patient-trial matching system of claim 1, wherein ranking the matched results using the ranking criteria includes applying a first-level priority to the ranked clinical trials based on a first criterion of the ranking criteria and a second-level priority to the ranked clinical trials based on a second criterion of the ranking criteria.

* * * * *